United States Patent
Niemann et al.

(10) Patent No.: US 10,598,745 B2
(45) Date of Patent: Mar. 24, 2020

(54) PERMANENT MAGNET ARRANGEMENT FOR MR APPARATUSES WITH AXIALLY AND LATERALLY DISPLACEABLE, ROTATABLY MOUNTED RING MODULES

(71) Applicant: Bruker BioSpin GmbH, Rheinstetten (DE)

(72) Inventors: Volker Niemann, Ispringen (DE); Rainer Pietig, Malsch (DE); Lukas Haenichen, Karlsruhe (DE)

(73) Assignee: BRUKER BIOSPIN GMBH, Rheinstetten (DE)

( * ) Notice: Subject to any disclaimer, the term of this patent is extended or adjusted under 35 U.S.C. 154(b) by 238 days.

(21) Appl. No.: 15/941,134

(22) Filed: Mar. 30, 2018

(65) Prior Publication Data

US 2018/0292481 A1  Oct. 11, 2018

(30) Foreign Application Priority Data

Mar. 31, 2017  (DE) .......................... 10 2017 205 485

(51) Int. Cl.
*G01R 33/383* (2006.01)
*H01F 7/02* (2006.01)
(Continued)

(52) U.S. Cl.
CPC .......... *G01R 33/383* (2013.01); *G01N 24/08* (2013.01); *G01R 33/307* (2013.01);
(Continued)

(58) Field of Classification Search
CPC ............... G01R 33/383; G01R 33/307; G01R 33/3873; G01N 24/08; H01F 7/0278; H01F 7/0284
See application file for complete search history.

(56) References Cited

U.S. PATENT DOCUMENTS 3,018,422 A * 1/1962 Seaton .................. H01F 7/0278
   335/298
3,646,669 A * 3/1972 Erickson ............... H01F 7/0278
   29/607

(Continued)

FOREIGN PATENT DOCUMENTS

EP  0479278 A1  10/1991
EP  1876462 A1  1/2008
(Continued)

OTHER PUBLICATIONS

Phuc et al., "Design and Construction of Light Weight Portable NMR Halbach Magnet", International Journal of Smart Sensing and Intelligent Systems, vol. 7, No. 4, Dec. 2014, 24 pages.

*Primary Examiner* — Mohamad A Musleh
(74) *Attorney, Agent, or Firm* — Edell, Shapiro & Finnan, LLC (57) ABSTRACT

A magnet arrangement (1) having a permanent magnet system with at least two ring-shaped magnet elements (2) which are made of individual magnet segments (3), are arranged cylindrically symmetrically and stacked on one another in the z direction and/or concentrically, and arranged such that the magnetization directions of the individual segments in the rings extend parallel in an x-y plane. The magnet elements align relative to one another in the z direction and have a Halbach magnetization Before final mounting in the magnetic resonance apparatus, the magnet elements are prefabricated as solid structures and their respective magnet segments are fixed undisplaceably relative to one another. But the magnet elements are displaceable relative to one another in the x-y plane, and are mounted rotatably and/or tiltably relative to one another.

21 Claims, 3 Drawing Sheets

(51) Int. Cl.
    *G01N 24/08*    (2006.01)
    *G01R 33/30*    (2006.01)
    *G01R 33/3873*  (2006.01)

(52) U.S. Cl.
    CPC ......... *H01F 7/0278* (2013.01); *H01F 7/0284* (2013.01); *G01R 33/3873* (2013.01)

(56) References Cited

U.S. PATENT DOCUMENTS

| | | | |
|---|---|---|---|
| 4,355,236 A | 10/1982 | Holsinger | |
| 4,862,128 A | 8/1989 | Leupold | |
| 4,931,760 A | 6/1990 | Yamaguchi et al. | |
| 5,014,032 A | 5/1991 | Aubert | |
| 6,011,396 A * | 1/2000 | Eckels | G01R 33/3806 324/300 |
| 6,573,817 B2 * | 6/2003 | Gottschalk | H05H 7/04 335/302 |
| 7,084,633 B2 | 8/2006 | Aoki et al. | |
| 7,986,205 B2 * | 7/2011 | Horisaka | A61B 1/041 324/319 |
| 8,077,002 B2 | 12/2011 | Lian et al. | |
| 8,643,454 B2 * | 2/2014 | Fullerton | G01D 18/00 335/285 |
| 2012/0013338 A1 | 1/2012 | Sakellariou et al. | |
| 2013/0207657 A1 | 8/2013 | Leskowitz et al. | |

FOREIGN PATENT DOCUMENTS

| | | |
|---|---|---|
| EP | 2144076 B1 | 1/2010 |
| JP | S61276308 A | 12/1986 |
| JP | H0283903 A | 3/1990 |
| JP | 2015513074 A | 4/2015 |

* cited by examiner

PERMANENT MAGNET ARRANGEMENT FOR MR APPARATUSES WITH AXIALLY AND LATERALLY DISPLACEABLE, ROTATABLY MOUNTED RING MODULES

CROSS REFERENCE TO RELATED APPLICATIONS

This application claims foreign priority under 35 U.S.C. § 119(a)-(d) to German Application No. 10 2017 205 485.9 filed on Mar. 31, 2017, the entire contents of which are hereby incorporated into the present application by reference.

FIELD OF THE INVENTION

The present invention relates in general to the field of magnetic resonance, in particular to the provision of permanent magnet systems suitable therefor, which are intended to generate homogeneous magnetic fields for NMR measurements. The applicability of the invention is not, however, restricted to this area.

BACKGROUND

A magnet arrangement in a magnetic resonance apparatus known in the art has a permanent magnet system for generating a homogeneous magnetic field in a direction perpendicular to a z axis in a measurement volume. This permanent magnet system includes at least 2, in particular at least 3, ring-shaped magnet elements made of magnetic material, which are arranged cylindrically symmetrically with respect to the z axis and stacked on one another in the z direction and/or concentrically. The ring-shaped magnet elements are made up of individual magnet segments and are arranged such that the magnetization direction of the individual segments in the respective rings extends essentially parallel in an x-y plane perpendicular to the z direction. The ring-shaped magnet elements respectively have a Halbach magnetization that generates a magnetic dipole field, and the ring-shaped magnet elements are alignable relative to one another in the z direction.

Such a magnet arrangement is known from EP 2 144 076 B1.

Both in the field of nuclear magnetic resonance (NMR) spectroscopy and in imaging applications (MRI), a very homogeneous magnetic field which is constant as a function of time is required in a sample volume to be defined. This field may be generated with resistive or superconducting coils or a suitable permanent magnet arrangement. The use of permanent magnets is preferred when flux densities of less than 2 T are sufficient and a relatively compact structure is desired.

In order to maximize the magnetic flux and the sample volume, and therefore at the same time to minimize the stray flux, the magnetic flux must be concentrated. In this case, distinction is made between magnetic circuits in which the magnetic return path is produced through a yoke of soft magnetic material, and magnetic circuits which make do without a yoke. The latter are usually variants of so-called Halbach magnets, in which the return flux is simplified by a gradual variation of the magnetization direction. In practice, a Halbach arrangement is typically achieved by a stepwise variation of the magnetization direction. This departure from the ideal Halbach magnetization, and in particular also the finite length of the Halbach arrangement, contribute to an increase of the stray field outside the magnet arrangement per se, and make additional shielding necessary for stray field-free applications. In the case of yoke-based magnets, sufficient shielding of the stray field can be achieved by skillful yoke design and use of the yoke material far below the saturation flux density.

In order to achieve the required field homogeneity in the sample volume, in the Halbach embodiments described it is generally necessary to provide correction mechanisms in order to be able to compensate for tolerances of the magnet material or of the positions of the individual magnet units, which complicates the mechanical structure.

One problem then consists in determining the dominant perturbing field orders and establishing a causal relationship with a corresponding adjustment mechanism.

Naturally, it is the case that any variation of the spatial arrangement of the magnets has an effect on all the field orders. Correspondingly, an arrangement in which all the magnet segments are adjustable degenerates into a "multidimensional" optimization problem with an enormous number of degrees of freedom. This means that the "result vector" for a particular "shim target" is very long; it would in essence be necessary to carry out correction on very many of these adjustment elements. Not only is this balancing process very time-consuming, but it is not a priori certain that such a procedure will in fact ever converge to an absolute optimum.

There are orders for which correction has a higher priority, predominantly the "zonal" terms and linear gradients. It is thus necessary to find geometrical variations which can be connected with the prioritized orders, preferably independently of one another. These variations should be as technically simple as possible to implement, since it is generally necessary to work against magnetic forces, and the adjustment precision in very complex movement procedures usually suffers, or its technical achievement becomes exorbitantly expensive. Linear movement and rotation can usually be carried out with manageable outlay.

The permanent magnets are typically held by a supporting structure, which may additionally fulfill the function of the magnetic return path. Traditional designs have a yoke in the form of a rectangular frame (window frame, H yoke, C yoke) with two central magnet modules lying opposite one another, between which the sample volume is located. Because of their open layout, these yoke designs also usually suffer from stray fields which extend far beyond the outer contours of the magnet arrangement.

In order to achieve the field homogeneity in the sample volume which is required for NMR measurements, in the case of yoke-free Halbach magnets it is necessary to provide correction mechanisms in order to be able to compensate for tolerances of the magnet material or the position of the individual magnet units, which complicates the mechanical structure. Yoke-based magnets generally have a parallel pole piece pair consisting of a soft magnetic material, with a correspondingly high saturation flux density. By suitable selection of the pole shoe geometry and special surface processing, the field profile can be optimized in a relatively simple and efficient way.

U.S. Pat. No. 8,077,002 B2 discloses a permanent magnet device for MRI applications. It comprises a pair of solid disk-like magnets, which delimit the air gap as a symmetry plane in a parallel manner and each have an offset (protruding) ring magnet, so that an L-shaped magnet is formed. Pole shoes are arranged on both sides of the air gap for parallel alignment of the magnetic field in the air gap. The so-called L-magnet arrangement is held by a T yoke. Since this magnet arrangement is an open structure, this T yoke is necessary because of the way it is designed. The T yoke sections described are connected by an additional strut as a magnetic return path.

U.S. Pat. No. 7,084,633 B2 discloses a magnet arrangement for MRT instruments using permanent magnets. The permanent magnets are arranged in such a way that a pair of central permanent magnets are respectively connected to a pole shoe, in the intermediate space of which the measurement volume is located. The magnetizations of the two magnets are oriented in the same direction, so that the magnetic flux flows in a defined direction through the measurement volume. Further segments of permanent magnets are arranged in the shape of a circle around said magnets, the magnetization directions of the magnets being directed radially outward or radially inward, so that the magnetic field inside the measurement volume is strengthened. Plates consisting of ferromagnetic material are arranged as a yoke for the return of the magnetic field. For design reasons and in order to guide the magnetic flux of the corner segments, supporting yokes are required at the respective corners.

US 2012/0013338 A1 discloses a magnet arrangement for magnetic resonance devices, which consists of at least two rings with different magnetization directions. In one embodiment, a central Halbach ring (see FIG. 13 therein) is arranged, which is flanked by two radially magnetized rings. The purpose of the known device is to obtain a magnetic field which is adjustable in the magnetization direction, and which can be varied from 0° to 90°, and in particular also around the magic angle of 54.7°. The magnet segments are likewise intended to be orientable, so that a maximally homogeneous field is formed in the measurement volume. A disadvantage with this, however, is the complicated structure, which is difficult to produce in practice.

EP 1 876 462 A1 discloses a stack of at least two magnet rings, which are arranged around a sample space and are mounted rotatably relative to one another. The individual rings preferably have a Halbach geometry. By rotation of the rings, it is possible to achieve a field sweep, such as is used in ESR technology. The focus of this arrangement is not to be able to vary the nominal strength of the magnetic field during operation, but to improve the homogeneity. To this end lateral displacements of the rings are essential, and although axial rotatability is provided it is only of secondary importance in this case. In EP 1 876 462 A1, a concentric arrangement is prescribed. By definition, there is concentricity when the midpoints are identical, but this is not the case for rings which are arranged along a common axis. The magnet groups described in EP 1 876 462 A1 are displaceable neither along the z axis nor transversely thereto. The only degree of freedom claimed is restricted to the mutual rotatability. This is possible in the known arrangement precisely because the magnet groups are arranged coaxially, i.e. they have the same rotation axis.

U.S. Pat. No. 4,355,236 and U.S. Pat. No. 4,862,128 also disclose permanent magnet rings in Halbach configuration (QUADRUPOLE) as a stack of a plurality of rings, which are mounted rotatably relative to one another so that the magnetic flux in the measurement volume can be varied. The rings are not, however, displaceable relative to one another eccentrically in the x-y plane, and also cannot be spaced apart in the z direction.

U.S. Pat. No. 4,355,236 describes a multipole magnet, and in particular reference is exclusively made to quadrupoles, the reason for which is the intended use as a focusing element for a charged particle beam. This is because quadrupoles constitute the best focusing element in particle accelerators (see also FODO structure).

To this end, the individual magnetic rings must be rotatable, in order to also be able to cancel a field when necessary, and rotatability even up to 45° is consequently necessary. Furthermore, the particle beam, in particular electron beam to be focused, is very small in comparison with a conventional MR measurement volume. Therefore, the requirements for the homogeneity of the arrangement according to U.S. Pat. No. 4,355,236 are also not nearly as demanding as in the case of an MR dipole. The magnet groups described in U.S. Pat. No. 4,355,236 are displaceable neither along the z axis nor transversely thereto. U.S. Pat. No. 4,355,236 it is therefore to be regarded as rather remote in relation to the generic arrangement defined in the introduction, especially because possible applications for NMR or EPR are not mentioned at all in U.S. Pat. No. 4,355,236.

The disclosure content, relevant for the present invention, of U.S. Pat. No. 4,862,128 is very similar to that of the above-described U.S. Pat. No. 4,355,236. U.S. Pat. No. 4,862,128 does not, however, define a particular field of application, but merely the "generation of a homogeneous magnetic field". The magnet groups here are also displaceable neither along the z axis nor transversely thereto. The point in question is a linear array, but not displaceability for producing or improving the homogeneity.

EP 2 144 076 B1, which was cited in the introduction, discloses a Halbach architecture consisting of three rings, a central magnet ring being flanked by two head rings. The rings are mutually displaceable in the longitudinal direction by using screws or threaded nuts for the purpose of field homogenization, as revealed by paragraphs [0021]-[0025] and [0040], as well as FIG. 7 therein. EP 2 144 076 B1 furthermore discloses that the rings consist of individual segments, which are alternately trapezoidal and rectangular, the individual segments being displaceable in the radial direction for field homogenization. This magnet is constructed according to EP 2 144 076 B1, and has 64 mechanical degrees of freedom. To adjust these is in any event quite difficult. Furthermore, the arrangement according to EP 2 144 076 B1 does not consist of Halbach rings premounted in a fixed fashion, which are produced from trapezoidal individual component parts. The rings are also not displaceable relative to one another in the transverse direction, or through rotational movement. A disadvantage is therefore that the structure and the mounting are very complicated and expensive. The arrangement is not even likely to achieve field strengths of 1.9 T, since, due to the mechanical structure, the entire volume cannot be used. Explicitly, EP 2 144 076 B1 in any case discloses merely a maximum field strength of 0.7 T.

SUMMARY

By contrast, one object of the present invention is therefore to provide, by simple technical measures and without an increase in volume, a permanent magnet arrangement of the type defined in the introduction for an MR device, which comprises a plurality of rings in Halbach configuration and is therefore substantially easier to mount, and therefore significantly more economical to produce. A further object is to minimize the magnetic field gradients due to mounting. A Halbach arrangement is therefore proposed which makes do with substantially fewer mechanical shim degrees of freedom.

These and other objects are achieved by the present invention, first, in that, before final mounting in the magnetic resonance apparatus, the ring-shaped magnet elements are prefabricated as solid structures and their respective magnet segments are fixed undisplaceably relative to one another, further in that the ring-shaped magnet elements are arranged displaceably relative to one another in the x-y plane, and furthermore in that the ring-shaped magnet elements are mounted rotatably and/or tiltably relative to one another.

The invention provides a magnet device which is constructed from rings of Halbach magnets, adhesively fixedly bonded. The manufacturing tolerances incurred, or the inhomogeneities resulting therefrom, are minimized by movement of the individual rings relative to one another.

The proposed magnet arrangement does not have a yoke, and consists of at least 2 ring-shaped segmented magnet modules, the magnetization of which approximates a Halbach scheme. The ring modules are adjustable relative to one another in a particular way. Since the ring modules as a whole are adjusted, rather than individual segments, the number of possible degrees of freedom is reduced to at most three per ring. Notably, the homogenization process is simplified by these few degrees of freedom.

This solution approach according to the invention is therefore aimed at combining the permanent magnet segments to form ring modules. Positioning of the rings relative to one another has the necessary degrees of freedom to be able to correct prioritized field orders by simple movement processes.

Thus, in the present invention, the central ring as a whole is adhesively fixedly bonded, and as a whole is laterally displaceable relative to the upper and lower rings. It is thus not individual segments that are displaced, but instead the entire central ring (2 degrees of freedom). In addition, even more mechanical degrees of freedom are incorporated: the height displacement and the rotation of the upper and lower rings (two degrees of freedom, respectively). There are thus only 6 mechanical degrees of freedom in this case. These are used primarily for shimming the linear gradients. In addition, a shim tube (in a similar way as in the known MRI magnets of the Applicant) is provided for shimming the higher field orders.

The background is the "ironless magnet, based on Halbach-like magnetization. There are already various published Halbach-like embodiments, the structures of which are usually connected with many individually adjustable magnet segments, which entails a relatively elaborate homogenization process. Very many degrees of freedom are possible.

The approach according to the invention reduces the whole to a plurality of ring modules, i.e. at least two segmented Halbach rings, although these are mounted slightly displaceably both axially and transversely, and in addition can be rotated relative to one another through a small angle.

Various embodiments are possible: inter alia, in the invention, three rings with different internal and external radii and thicknesses are currently used. The ring modules do not naturally "float" freely in space, but have a holding structure and elements for fixing the position, although these will not be described in detail here. With this concept according to the invention, an arrangement that can be homogenized with reasonable outlay is obtained, which has not yet existed. The structure with independent ring modules also provides advantages for mounting.

The magnetic components are furthermore safeguarded by the structure according to the invention against undesired movements. Because of the geometrical shape, neighboring components prevent undesired movement in the mounted state. Because of the form-fit arrangement of the magnet modules, intrinsic security of the system is obtained.

The rotationally symmetrical structure, because of the cylindrical geometry, optimally matches the shape of the measurement module, so that use of material is substantially more efficient because of the shorter average magnetic circuit length compared with rectangular arrangements.

Reduction of the usually large number of degrees of freedom to a minimum, which nevertheless allows effective mechanical shimming.

Mechanical assembling of the individual ring modules without further complicated adjustment mechanisms such as mobile magnets, shunts and the like.

Rotational symmetry: the chassis components can therefore be manufactured on a simple turning machine. Furthermore, convenient sequential mounting on a turning platform is made possible.

Security: intrinsic security by form-fit arrangement of the magnet modules and the yoke parts. In the assembled state, all the magnets are secured against relative movements.

Particularly preferred is an embodiment of the magnet arrangement according to the invention in which the ring-shaped magnet elements are mounted rotatably about the z axis. Production-related variations of the segments assembled in the shape of a ring may cause an angle deviation of the magnetic axis of an entire ring. By the embodiment described, this angle deviation can be corrected by adjusting a corresponding angle in the counter sense.

Further advantageous embodiments are characterized in that the ring-shaped magnet elements are arranged concentrically about the z axis, and in that the radially outer ring-shaped magnet elements are mounted in a fixed relative positioning, and the radially inner ring-shaped magnet element is mounted to be moveable. In order to homogenize the magnets, inter alia linear field gradients transverse to the z axis must be minimized. Because of the mobile mounting of the central magnet ring, there is a possibility for influencing above all linear gradients. Because only a part of the magnet mass can be moved, a finer resolution of the achievable adjustment range is obtained. Furthermore, the stationary part provides the required bearing and guiding face for the mobile part and has the necessary pulling or pushing mechanisms for fixing the end position.

According to a further advantageous embodiment, the ring-shaped magnet elements are arranged concentrically about the z axis, and the radially inner ring-shaped magnet element has a higher coercive field strength than the radially outer ring-shaped magnet elements. According to the magnetic field strengths inside the segments contained in the magnet arrangement, irreversible demagnetization effects may occur according to the coercive field strength of the magnet material used, which would make the apparatus unusable. This can be prevented by using a material with a correspondingly high coercive field strength. Since materials with a high coercivity typically have a lower remanence, a combination of high-remanence material (towards larger radii) with high-coercivity material (towards smaller radii) is most effective in relation to the total use of material.

One preferred embodiment is characterized in that the ring-shaped magnet elements are arranged stacked on one another in the z direction, in that the permanent magnet system comprises at least 3 ring-shaped magnet elements, and in that the central ring-shaped magnet element as a whole is adhesively fixedly bonded and as a whole is displaceable laterally relative to the upper and lower ring-shaped magnet elements. This arrangement makes it possible to mount the individual ring modules (optionally consisting of different materials) as self-contained modules and provides the minimum number of mechanical degrees of freedom required for the homogenization.

Also advantageous is an embodiment in which the ring-shaped magnet elements are arranged stacked on one another in the z direction, and in which the central ring-shaped magnet element is mobile only in the x-y plane and the upper and lower ring-shaped magnet elements are displaceable and rotatable in the z direction. With this combination, the required displacement paths for the homogenization is achieved with a minimum of mechanical degrees of freedom. The field orders thereby influenced are in this case substantially decoupled from one another, which significantly simplifies the homogenization process. See above: for example, almost exclusively linear field gradients are influenced by the transverse offset of the central ring module.

A further advantageous embodiment of the magnet arrangement according to the invention is distinguished in that the ring-shaped magnet elements are arranged stacked on one another in the z direction, and in that the central ring-shaped magnet element is made up of two concentric magnet rings, which are fastened with respect to one another, preferably with struts, so that holes for insertion of correction elements or shim structures remain between the rings. Apart from the described mechanical degrees of freedom, these holes additionally provide a possibility of carrying out more complex corrections, for example by introducing additional magnet material. According to the configuration of these shim structures, very finely resolved displacement paths can be achieved.

Particularly preferred is an embodiment in which the ring-shaped magnet elements are arranged stacked on one another in the z direction, and the central ring-shaped magnet element is mounted floating in the x-y plane, holding devices, in particular sliding blocks, being provided, which protrude through openings in the housing device and with which the X-Y position of the central ring-shaped magnet element can be adjusted. The concentric arrangement of the ring modules means that the inner-lying modules are no longer externally accessible. Only by the sliding blocks and/or further connecting elements are the access points for the position adjustment of the central ring module transferred through wall openings onto the outer circumference, and adjustability is thus made possible.

Especially preferred is an embodiment of the invention in which a device for homogenizing the magnetic field is provided, preferably a shim tube for shimming the higher field orders. The mechanisms described above are in this way supplemented by a further, even more precise instrument for homogenization. Even more finely resolving corrections are therefore possible.

One class of particularly preferred embodiments of the magnet arrangement according to the invention is distinguished in that the permanent magnet system is bounded on both sides in the direction of the z axis by two cover modules, each of which comprises a ring-shaped magnet element and a cover component with which the ring-shaped magnet elements can be rotated on a housing device, can be displaced in the z direction and can be fastened on the housing device. The composition of the magnet material is unsuitable for receiving fastening elements, such as screw threads or the like. In order to offer secure holding for the magnet segments and to provide surfaces for the fastening of mechanical holding and adjustment devices, the partial mounting is carried out in the described cover modules, which furthermore receive the devices for rotating and fixing the rotatably mounted modules, and contain pressure/bracing elements for the spacing adjustment along the z axis.

Advantageous refinements of this class of embodiments are characterized in that positioning elements, in particular adjustment screws, are provided, with which the cover modules can be tilted out of the x-y plane and/or can be rotated about the z axis relative to the housing device. By asymmetric adjustment of the positioning elements, a slight inclination/tilting of the ring modules can be adjusted, in order in turn to compensate for asymmetries of the modules themselves.

The scope of the present invention also includes a method for producing a magnet arrangement according to the embodiment described above, or its refinement, comprising:
(a) adhesively bonding the premagnetized magnet segments to form magnet rings, preferably inside a holding ring;
(b) producing a central magnet ring module by introducing a magnet ring into a central ring-shaped housing device having at least two openings, and fastening the magnet ring by holding devices, which are mounted on the magnet ring through the openings in the housing device, so that the magnet ring is mounted to float in the housing device;
(c) fitting a guide arrangement on the central magnet ring module and on the cover modules, and joining together the magnet rings against the repulsion forces of the magnets;
(d) fixing the cover components on the housing device;
(e) iteratively measuring the field homogeneity and adjusting the position of the magnet rings with respect to one another with the aid of positioning elements; and
(f) removing the guide arrangement.

In the case of mounting already magnetized permanent magnets, attraction and repulsion forces of the order of several tonnes occur. These forces must be braced or absorbed during fitting, in order to bring the magnet elements securely into the intended positions. This is particularly readily possible with the mounting method described here.

Preferably, mutually opposite through-holes are used so that the magnet ring is more mobile in the housing. Also suitable, however, are three openings which do not lie opposite one another.

The guide arrangement in step (c) is used to prevent transverse movements. This may, for instance, be achieved by one or more rail(s) or bar(s). By definition, however, a rail has no further degrees of freedom for rotating the central ring if necessary into the end position in an alternative configuration of the invention.

Preferably, the modules are fitted on the guide arrangement in such a way that one module is connected to be fixed to the guide arrangement and the other two modules are provided with sliding bushes. Using a push or pull device, the outer modules are moved toward one another along the z axis, the central module lying between them remaining mobile along the z axis. Because of the symmetry of the arrangement, and the consequent symmetry of the repulsion forces, the central module is always positioned at the same distance from the two outer modules. This allows a uniform joining process and symmetrical gap dimensions until the end position is reached. The magnet rings may, for example, be joined together with the aid of a spindle.

The iterative measurement of the field homogeneity and the adjustment of the position of the central ring in the x-y plane in step (e) is preferably carried out using tension and pressure screws or pressure springs, likewise the adjustment of the separation of the two cover modules, and homogenization of the field by rotation of the cover modules.

In one advantageous variant of the method according to the invention, before the adjustment of the field homogeneity in step (e), as an alternative an outer bridge is fitted on the housing device. Subsequently, the cover module is separated from the housing device, so that the cover modules are mounted displaceably and rotatably relative to the central magnet ring module.

According to another preferred method variant, after the adjustment of the field homogeneity in step (e), spacers are introduced where gaps are intended to be left between the magnet rings.

Lastly, the scope of the present invention also includes a method for homogenizing the magnetic field of an above-described magnet arrangement, comprising the following steps:
adjusting the magnet rings as entire rigid modules;
improving the homogeneity of the magnetic field in the measurement volume by lateral displacement of the rings and/or tilting relative to the z axis and/or rotation about the z axis.

Other advantages of the invention may be found in the description and the drawing. Likewise, the features mentioned above and those referred to below may be used according to the invention in each case independently, or several of them may be used in any desired combinations. The embodiments shown and described are not to be interpreted as an exhaustive list, but rather have an exemplary nature for the description of the invention.

BRIEF DESCRIPTION OF THE DRAWING

The invention is represented in the figures and diagrams of the drawing, and will be explained in more detail with the aid of exemplary embodiments.

DETAILED DESCRIPTION

The magnet arrangement 1 according to the invention, as represented in the figures of the drawing in various embodiments, in each case schematically, has its main use as a component part of a magnetic resonance apparatus. Such a magnetic resonance apparatus, not represented separately in the drawing, has a permanent magnet system for generating a homogeneous magnetic field in the direction of a z axis in a measurement volume 0 (indicated in FIG. 1B), the permanent magnet system comprising at least two, in particular at least three, ring-shaped magnet elements 2 made of magnetic material, which are arranged cylindrically symmetrically with respect to the z axis and stacked on one another in the z direction and/or concentrically. The ring-shaped magnet elements 2 are made up of individual magnet segments 3 and arranged so that the magnetization directions of the individual segments in the respective rings extend essentially parallel in an x-y plane perpendicular to the z direction. In addition, the ring-shaped magnet elements 2 respectively have a Halbach magnetization that generates a magnetic dipole field, and, furthermore, the ring-shaped magnet elements 2 are aligned relative to one another in a plurality of degrees of freedom.

In general, the magnet arrangement 1 according to the present invention is distinguished in that, before final mounting in the magnetic resonance apparatus, the ring-shaped magnet elements 2 are already prefabricated as solid structures such that respective magnet segments 3 are fixed undisplaceably relative to one another, in that the ring-shaped magnet elements 2 are arranged displaceably relative to one another in the x-y plane, and in that the ring-shaped magnet elements 2 are mounted rotatably and/or tiltably relative to one another.

Preferably, the ring-shaped magnet elements 2 are mounted rotatably about the z axis.

The ring-shaped magnet elements 2 are preferably arranged concentrically about the z axis, the radially outer ring-shaped magnet elements 5 being mounted in a fixed relative positioning, and the radially inner ring-shaped magnet element 4 being mounted to be moveable, or vice versa.

Also, the ring-shaped magnet elements 2 are preferably arranged concentrically about the z axis, the radially inner ring-shaped magnet element 4 having a higher coercive field strength than the radially outer ring-shaped magnet elements 5.

In embodiments of the invention, the ring-shaped magnet elements 2 are arranged stacked on one another in the z direction. The permanent magnet system then comprises at least three ring-shaped magnet elements 2, as can be seen clearly in FIGS. 1A, 1B and 2. The central ring-shaped magnet element 8—as represented in FIGS. 3B and 4—as a whole is adhesively fixedly bonded there and as a whole is displaceable laterally relative to the upper and lower ring-shaped magnet elements.

The ring-shaped magnet elements 2 is preferably arranged stacked on one another in the z direction, as shown in FIGS. 1A to 3A and 5. In simpler refinements the central ring-shaped magnet element 8 may then be configured such that it is mobile only in the x-y plane, while the upper and lower ring-shaped magnet elements are also displaceable and rotatable in the z direction.

Figure 3A:
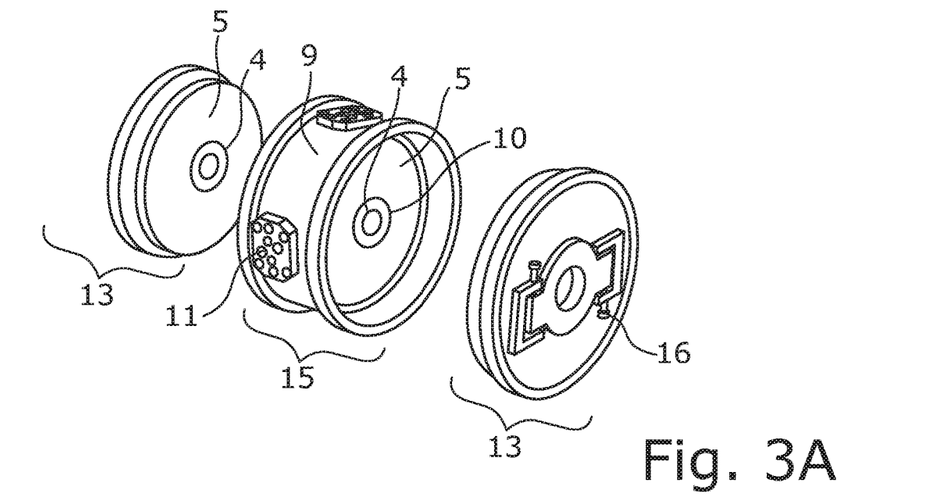
FIG. 3A shows a schematic three-dimensional representation of one embodiment of the magnet arrangement according to the invention with six Halbach rings in an arrangement stacked along the z direction as an exploded representation in the disassembled state.
Figure 3B:
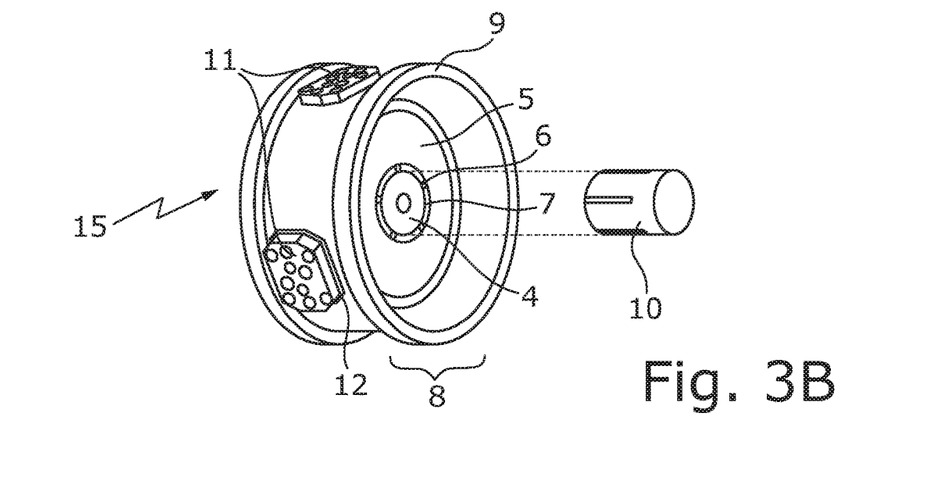
FIG. 3B shows a central magnet arrangement of FIG. 3A with a shim tube.
Figure 4:
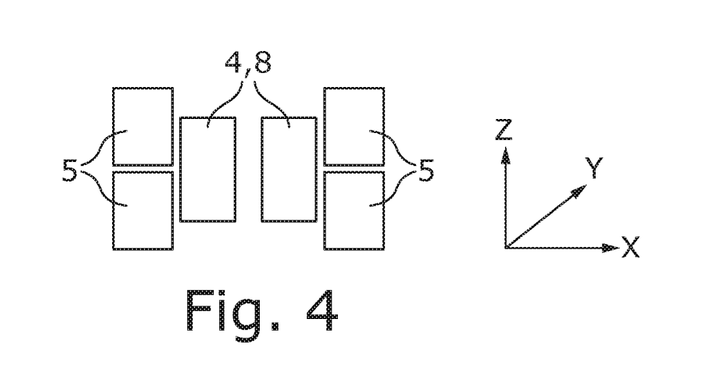
FIG. 4 shows a schematic vertical section through one embodiment with ring elements arranged coaxially around the z axis.
Figure 5:
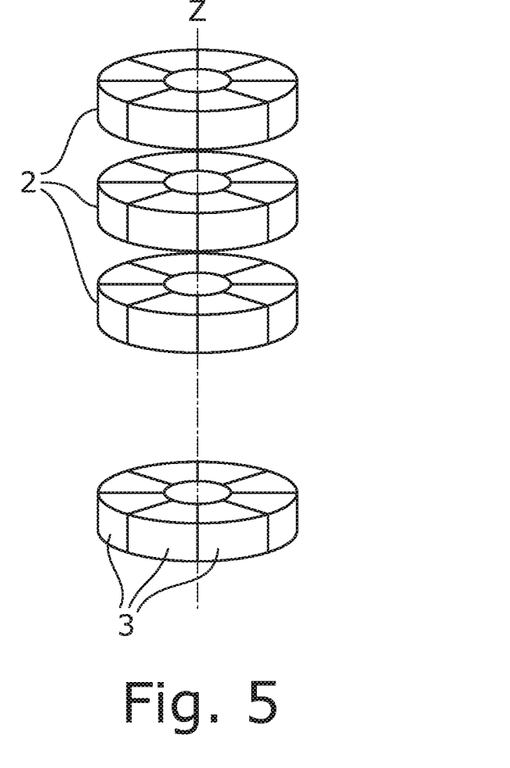
FIG. 5 shows an outlined embodiment with more than three segmented ring elements arranged on the z axis, as an exploded representation in the disassembled state.
Figure 6:
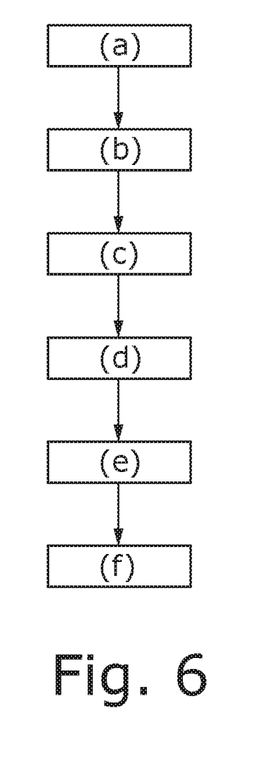
FIG. 6 shows a flow chart of the method steps during the production of a magnet according to the invention.

The central ring-shaped magnet element 8 is also preferably made up of two concentric magnet rings 4,5, as can be seen clearly in FIGS. 3A, 3B and 4, for example. These are fastened with respect to one another—preferably with struts 6, as represented in FIG. 3B—so that holes 7 for insertion of correction elements 10 for homogenizing the magnetic field, for example shim structures such as a shim tube for shimming the higher field orders, remain between the rings.

Figure 2:
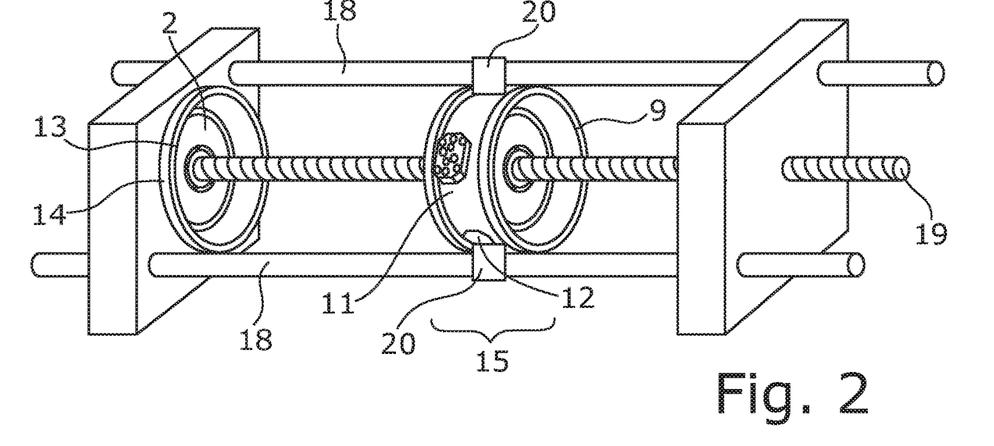
FIG. 2 shows a schematic three-dimensional overall view of a further embodiment of the magnet arrangement according to the invention and of one embodiment of the guide arrangement required for the mounting.

The central ring-shaped magnet element 8 is preferably mounted floating in the x-y plane, holding devices 11, in particular sliding blocks, being provided, which protrude through openings 12—indicated in FIG. 2—in the housing device 9 and with which the X-Y position of the central ring-shaped magnet element 8 can be adjusted. The adjustment of the X-Y position is carried out with positioning elements (not depicted in the figure), for example in the form of tension or pressure screws in the sliding blocks.

FIGS. 1A to 3A represent embodiments which are distinguished in that the permanent magnet system is bounded on both sides in the direction of the z axis by two cover modules 13. Each of the cover modules 13 comprises a ring-shaped magnet element 2 and a cover component 14 with which the ring-shaped magnet elements 2 can be rotated on a housing device 9, can be displaced in the z direction and can be fastened on the housing device 9. The cover modules 13 and the cover component 14 are in this case respectively adjacent axially to a central magnet ring module 15.

In general, in the magnet arrangement 1 according to the invention, positioning elements 16 are provided, and in particular adjustment screws in various geometrical embodiments and spatial placements, with which the cover modules 13 can be tilted out of the x-y plane and/or can be rotated about the z axis relative to the housing device 9.

Figure 1A:
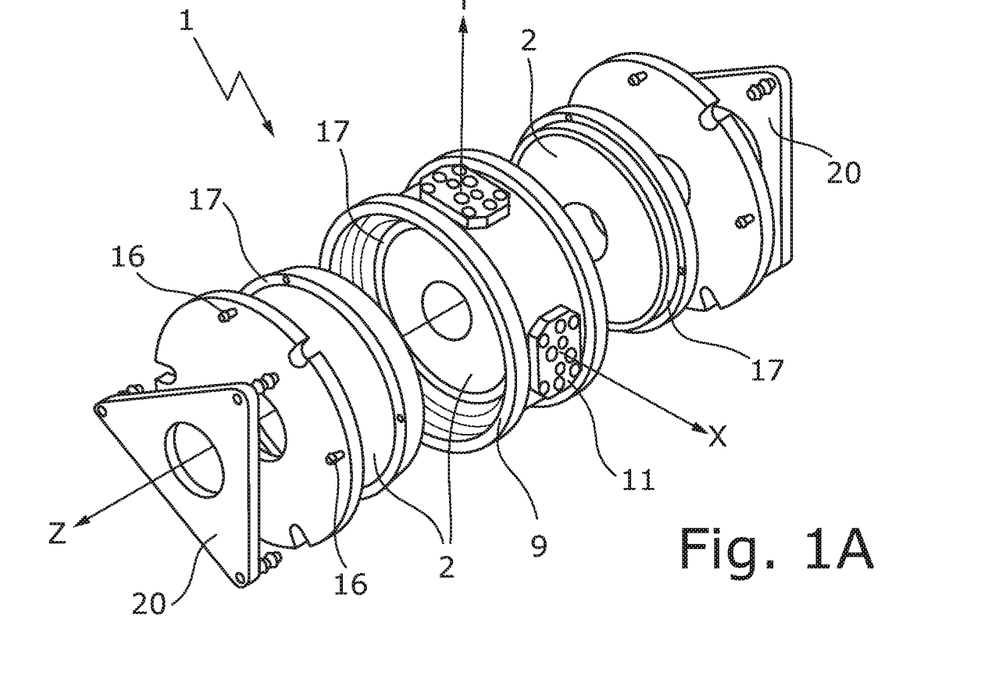
FIG. 1A shows a schematic three-dimensional exploded representation of one embodiment of the magnet arrangement according to the invention.
Figure 1B:
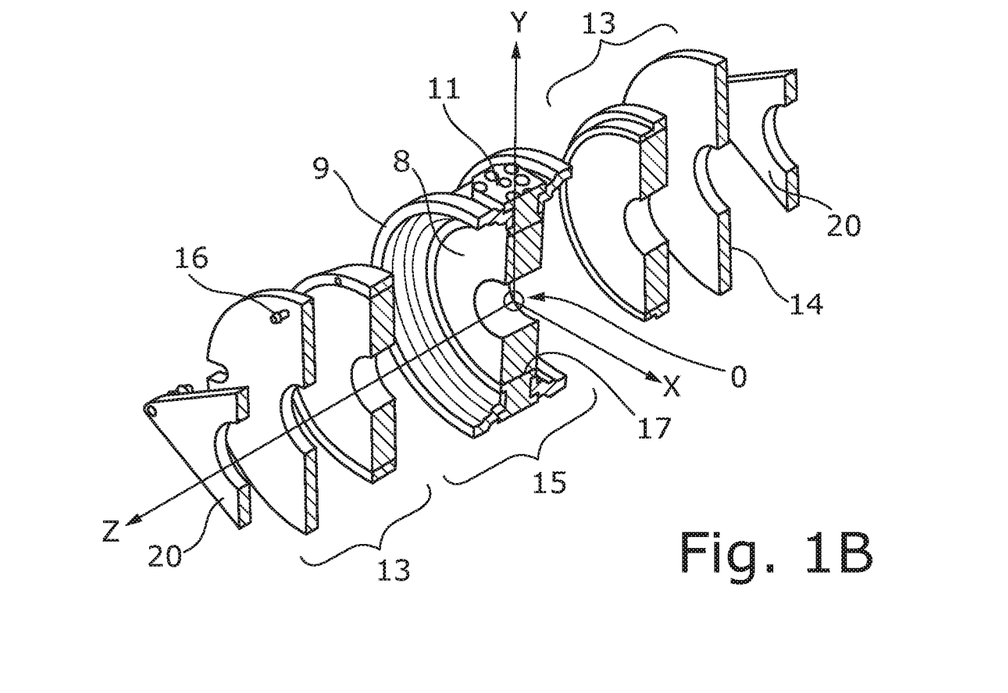
FIG. 1B shows the same as 1A, but as a half-section.

FIGS. 1A and 1B also show holding rings 17, inside which the magnet rings 2 are arranged.

FIG. 2 shows an arrangement for mounting a magnet arrangement according to the invention, with a guide arrangement 18 and a spindle 19, which are fitted on the central magnet ring module 15 and on the cover modules 13 in order to make it readily possible to join the magnet rings 2 together even against the repulsion forces of the magnets. The guide arrangement 18 and the spindle 19 are removed again after mounting. As an alternative to the spindle 19, it is also possible to use for example a hydraulic press or the like.

Before the adjustment of the field homogeneity, an outer bridge 20 is preferably fitted on the housing device 9. Subsequently, the cover module 13 is separated from the housing device 9, so that the cover modules 13 are mounted displaceably and rotatably relative to the central magnet ring module 15. As can be seen in FIG. 1A, with the aid of the bridge 20 the cover module 13 is fastened on the housing 9 so that the cover module 13 has sufficient play inside the bridge for the cover module 13 to be rotatable or tiltable about the z axis.

After the adjustment of the field homogeneity—not represented separately in the drawing—spacers are introduced in each case at the locations where gaps are intended to be left between the magnet rings 2.

The magnetic field of a magnet arrangement 1 according to the invention can be homogenized by adjusting the magnet rings 2 as entire rigid modules 13,15—as represented in FIGS. 1A to 2. For further improvement of the homogeneity of the magnetic field in the measurement volume 0, lateral displacements of the magnet rings 2 and/or tilts relative to the z axis and/or rotations about the z axis can be carried out.

LIST OF REFERENCES 0. measurement volume
1. magnet arrangement
2. ring-shaped magnet elements
3. magnet segments
4. radially inner ring-shaped magnet element
5. radially outer ring-shaped magnet element
6. struts
7. holes for shims
8. central ring-shaped magnet element
9. housing device
10. correction elements
11. holding devices
12. openings
13. cover modules
14. cover component
15. central magnet ring module
16. positioning elements
17. holding ring
18. guide arrangement
19. spindle
20. bridge

What is claimed is:

1. A magnet arrangement in a magnetic resonance apparatus, having a permanent magnet system for generating a homogeneous magnetic field in a direction perpendicular to a z axis in a measurement volume, the permanent magnet system comprising:
at least three ring-shaped magnet elements made of magnetic material, which are arranged cylindrically symmetrically with respect to the z axis and stacked on one another in the z direction and/or concentrically,
wherein the ring-shaped magnet elements are configured of individual magnet segments and are arranged such that the magnetization directions of the individual segments in the respective rings extend at least essentially parallel in an x-y plane perpendicular to the z direction,
wherein the ring-shaped magnet elements respectively have a Halbach magnetization that generates a magnetic dipole field,
wherein the ring-shaped magnet elements are configured to align relative to one another in the z direction,
wherein the ring-shaped magnet elements are prefabricated as solid structures prior to being mounted in the magnetic resonance apparatus such that respective magnet segments of the ring-shaped magnet elements are fixed undisplaceably relative to one another,
wherein the ring-shaped magnet elements are arranged displaceably relative to one another in the x-y plane, and
wherein the ring-shaped magnet elements are mounted rotatably and/or tiltably relative to one another.

2. The magnet arrangement as claimed in claim 1, wherein the ring-shaped magnet elements are mounted rotatably about the z axis.

3. The magnet arrangement as claimed in claim 1, wherein the ring-shaped magnet elements are arranged concentrically about the z axis, and wherein radially outer ones of the ring-shaped magnet elements are mounted in fixed relative positioning, and a radially inner one of the ring-shaped magnet elements is mounted to be moveable.

4. The magnet arrangement as claimed in claim 1, wherein the ring-shaped magnet elements are arranged concentrically about the z axis, and wherein radially outer ones of the ring-shaped magnet elements are mounted to be moveable, and a radially inner one of the ring-shaped magnet elements is mounted in a fixed position.

5. The magnet arrangement as claimed in claim 1, wherein the ring-shaped magnet elements are arranged concentrically about the z axis, and wherein a radially inner one of the ring-shaped magnet elements has a higher coercive field strength than radially outer ones of the ring-shaped magnet elements.

6. The magnet arrangement as claimed in claim 1, wherein the ring-shaped magnet elements are arranged stacked on one another in the z direction, wherein the permanent magnet system comprises exactly three ring-shaped magnet elements, and wherein a central one of the ring-shaped magnet elements as a whole is adhesively fixedly bonded and as a whole is displaceable laterally relative to upper and lower ones of the ring-shaped magnet elements.

7. The magnet arrangement as claimed in claim 1, wherein the ring-shaped magnet elements are arranged stacked on one another in the z direction, and wherein a central one of the ring-shaped magnet elements is mobile only in the x-y plane and upper and lower ones of the ring-shaped magnet elements are displaceable and rotatable in the z direction.

8. The magnet arrangement as claimed in claim 1, further comprising correction elements configured to homogenize the magnetic field.

9. The magnet arrangement as claimed in claim 8, wherein the correction elements comprise shim structures configured to shim the higher field orders.

10. The magnet arrangement as claimed in claim 9, wherein the shim structures comprise a shim tube.

11. The magnet arrangement as claimed in claim 1, wherein the ring-shaped magnet elements are arranged stacked on one another in the z direction, and wherein a central one of the ring-shaped magnet elements is configured of two concentric magnet rings, which are fastened with respect to one another such that holes for insertion of correction elements configured to homogenize the magnetic field are provided between the rings.

12. The magnet arrangement as claimed in claim 11, wherein the two concentric magnet rings are fastened with respect to one another with struts.

13. The magnet arrangement as claimed in claim 1, further comprising a housing device and holding devices, wherein the ring-shaped magnet elements are arranged stacked on one another in the z direction, and wherein a central one of the ring-shaped magnet elements is mounted floating in the x-y plane, wherein the holding devices protrude through openings in the housing device and are configured to adjust the X-Y position of the central ring-shaped magnet element.

14. The magnet arrangement as claimed in claim 13, wherein the holding devices are configured as sliding blocks.

15. The magnet arrangement as claimed in claim 1, further comprising two cover modules together bounding the permanent magnet system on both sides of the system in the direction of the z axis, and a housing device, wherein each of the modules comprises a ring-shaped magnet element and a cover component, wherein the cover component is configured to support the ring-shaped magnet elements to rotate on the housing device, to displace in the z direction on the housing device, and to be fastened onto the housing device.

16. The magnet arrangement as claimed in claim 15, further comprising positioning elements configured to tilt the cover modules out of the x-y plane and/or to rotate the cover modules about the z axis, relative to the housing device.

17. The magnet arrangement as claimed in claim 16, wherein the positioning elements comprise adjustment screws.

18. A method for producing a magnet arrangement as claimed in claim 15, comprising:
  (a) adhesively bonding the magnet segments, which are premagnetized, to form magnet rings;
  (b) producing a central magnet ring module by introducing one of the magnet rings into the housing device, which is centrally positioned in the magnet arrangement and is ring-shaped, and has at least two openings, and fastening the one magnet ring with holding devices which are mounted on the one magnet ring through the openings in the housing device, whereby the one magnet ring is mounted to float in the housing device;
  (c) fitting a guide arrangement on the central magnet ring module and on the cover modules, and joining together the magnet rings against the repulsion forces of the magnets;
  (d) fixing the cover components on the housing device;
  (e) iteratively measuring field homogeneity and adjusting positions of the magnet rings with respect to one another with the aid of positioning elements; and
  (f) removing the guide arrangement.

19. The method as claimed in claim 18, further comprising:
  prior to the iterative measuring of the field homogeneity and the adjusting of the positions of the magnet rings, fitting an outer bridge on the housing device and subsequently separating the cover modules from the housing device, so that the cover modules are mounted displaceably and rotatably relative to the central magnet ring module.

20. The method as claimed in claim 18, further comprising:
  subsequent to the iterative measuring of the field homogeneity and the adjusting of the positions of the magnet rings, introducing spacers where gaps are to be left between the magnet rings.

21. A method for homogenizing the magnetic field of a magnet arrangement as claimed in claim 1, comprising:
  adhesively bonding the magnet segments, which are premagnetized, to form magnet rings
  adjusting the magnet rings as entire rigid modules;
  improving the homogeneity of the magnetic field in the measurement volume by laterally displacing the rings and/or tilting the rings relative to one another.

* * * * *